United States Patent
Castor et al.

(10) Patent No.: US 6,955,790 B2
(45) Date of Patent: Oct. 18, 2005

(54) APPARATUS FOR PLASMA-CHEMICAL PRODUCTION OF NITROGEN MONOXIDE

(75) Inventors: Rolf Castor, Haegersten (SE); Thomas Hammer, Hemhofen (DE)

(73) Assignee: Maquet Critical Care AB, Solna (SE)

( * ) Notice: Subject to any disclaimer, the term of this patent is extended or adjusted under 35 U.S.C. 154(b) by 753 days.

(21) Appl. No.: 09/853,470

(22) Filed: May 11, 2001

(65) Prior Publication Data

US 2001/0031230 A1 Oct. 18, 2001

Related U.S. Application Data

(62) Division of application No. 09/320,045, filed on May 26, 1999, now Pat. No. 6,296,827.

(30) Foreign Application Priority Data

May 27, 1998 (DE) .......................................... 198 23 748

(51) Int. Cl.[7] .............................................. B01J 19/08
(52) U.S. Cl. .................................. 422/186.04; 423/405
(58) Field of Search ...................... 422/186.04; 423/405

(56) References Cited

U.S. PATENT DOCUMENTS

| 3,666,408 A | 5/1972 | Grosse et al. |
|---|---|---|
| 4,267,027 A | 5/1981 | Amouroux et al. |
| 4,287,040 A | 9/1981 | Alamaro |
| 4,399,012 A | 8/1983 | Chen |
| 4,451,436 A | 5/1984 | O'Hare |
| 4,877,589 A | 10/1989 | O'Hare |
| 5,843,383 A | * 12/1998 | Williamson et al. ... 422/186.04 |
| 5,914,015 A | * 6/1999 | Barlow et al. .............. 204/177 |

FOREIGN PATENT DOCUMENTS

| DE | 438 309 | 12/1926 |
|---|---|---|
| DE | 27 36 086 | 2/1978 |
| WO | WO 97/03746 | * 2/1997 |

OTHER PUBLICATIONS

International Publication No. WO 97/03746 (Hammer et al.), dated Feb. 6, 1997.
International Publication No. WO 95/07619 (Jacobsen), dated Mar. 23, 1995.

* cited by examiner

*Primary Examiner*—Kishor Mayekar
(74) *Attorney, Agent, or Firm*—Laurence A. Greenberg; Werner H. Stemer; Ralph E. Locher

(57) ABSTRACT

A method and an apparatus for plasma-chemical production of nitrogen monoxide is used to produce inhalation gas enriched with nitrogen monoxide for medical purposes. The nitrogen-monoxide production is achieved through the use of a dielectric barrier discharge created in a process gas containing nitrogen and oxygen.

11 Claims, 3 Drawing Sheets

APPARATUS FOR PLASMA-CHEMICAL PRODUCTION OF NITROGEN MONOXIDE

CROSS-REFERENCE TO RELATED APPLICATION

This is a division of U.S. application Ser. No. 09/320,045, filed May 26, 1999 now U.S. Pat. No. 6,296,827.

BACKGROUND OF THE INVENTION

FIELD OF THE INVENTION

The invention relates to an apparatus for plasma-chemical production of nitrogen monoxide (NO), in particular for medical purposes.

Nitrogen monoxide is a biologically important molecule for intracellular and intercellular transmission of impulses and for immunological reactions, which is normally also formed in the human body. The relief of stress in blood vessels is influenced by NO in the same way as the relief of stress in the alveoli or the smooth musculature in the gastric region. Conversely, a lack of NO can lead to the relaxation of the smooth musculature being suppressed, and thus to constrictions occurring. Such a constriction is evident, for example, in the bronchial area in the form of asthma. Many of those symptoms can be overcome, as is known, by inhalation of gas mixtures containing NO, with NO concentrations in the range of 0.5 ppm to 200 ppm.

Until now, such an inhalation gas containing NO has been obtained from gas cylinders, the storage and handling of which in a clinic or some other therapy facility is complex due to the safety measures required. That applies in particular to a mobile apparatus. Furthermore, the quality of the stored gas has to comply with stringent requirements for medical applications. Those requirements further increase the cost for production and storage. Specifically, even a minor impurity in the gas leads to the formation of undesirable, and possibly toxic, byproducts.

International Publication No. WO95/07610 discloses a method for plasma-chemical production of NO, in which NO is produced under the influence of a corona discharge in a process gas containing nitrogen ($N_2$) and oxygen ($O_2$). The corona discharge is operated continuously. A gas discharge of the described type disadvantageously leads to only a comparatively minor heating of the process gas to a temperature which is on the order of magnitude of 200° C. That comparatively low temperature only allows NO to be produced in a gas mixture with low efficiency. In fact, the $NO_2$ (which is undesirable for inhalation purposes) is preferentially produced. In order to remove the $NO_2$ from the inhalation gas, it is necessary to use a costly absorber technique. The disadvantage of an absorber is, in particular, that the absorber material must be replaced or reconditioned frequently.

A further method of that type is disclosed in U.S. Pat. No. 5,396,882. In that case, the plasma is produced through the use of a spark discharge (or else an arc discharge) instead of by the corona discharge. The spark discharge is highly energetic in comparison to a corona discharge and produces a comparatively large amount of gas heating, as a result of which correspondingly efficient NO production is achieved. However, the high thermal load on the electrodes, particularly at the spark contact point, disadvantageously leads to severe electrode erosion, that is to say to progressive decomposition of the electrode material. Due to that electrode erosion, the known method on one hand requires intensive maintenance since the electrodes are highly susceptible to wear. On the other hand, it is necessary to prevent the eroded electrode material, which is finely distributed in the inhalation gas, from reaching a patient's breathing passages. That requires complex cleaning of the inhalation gas.

The prior art also discloses other non-thermal gas discharges, for example dielectric barrier discharges, as other alternatives to a corona discharge or spark discharge. For example, German Patent No. 438309 describes a device for carrying out chemical reactions with the aid of high-voltage currents using outer electrodes which are covered with semiconductors, and a thin wire as an inner electrode that is also referred to as a corona electrode, in the case of which additives to achieve a catalytic effect are also added to the reaction mixture. However, that device is not suitable for producing pure nitrogen monoxide. That is because corona electrodes operate at low current densities and are therefore unsuitable for injecting sufficiently high electrical power levels for NO production, and the addition of a catalyst to the reaction gas mixture must, in principle, be regarded with apprehension for medical applications.

SUMMARY OF THE INVENTION

It is accordingly an object of the invention to provide an apparatus for plasma-chemical production of nitrogen monoxide, which overcome the hereinafore-mentioned disadvantages of the heretofore-known apparatuses of this general type and which are particularly effective.

With the foregoing and other objects in view there is provided, in accordance with the invention, a method for plasma-chemical production of nitrogen monoxide, which comprises passing a process gas containing nitrogen and oxygen through a discharge zone within which a dielectric barrier or impended gas discharge is created; and using the gas discharge to produce a non-thermal plasma with a gas temperature of at least 400° C. The dielectric barrier gas discharge leads to ionization of gas molecules, and thus to the formation of reactive radicals in the so-called non-thermal plasma. The gas discharge and thus the plasma production take place at the elevated gas temperature of at least 400° C.

The invention is based in this case on the concept that electrode erosion can be effectively avoided if the gas discharge is operated in brief discharge pulses rather than continuously. The dielectric barrier discharge is particularly suitable for this purpose since, in principle, it includes a series of short discharge pulses. A pulsed gas discharge caused by shortening the pulses of the discharge voltage would actually be unsuitable for achieving the object since a technically complex, and thus expensive, voltage supply would be required for that purpose. The voltage supply required to operate a dielectric barrier discharge can, in contrast, be produced easily and cost-effectively.

In this case, the NO production takes place sufficiently efficiently at a comparatively elevated temperature of at least 400° C. to 800° C., while undesirable nitrogen oxides in different oxidation states, for example $NO_2$, are produced only to a minor extent at the same time. In accordance with another mode of the invention, experiments have shown that a temperature range from 600° C. to 800° C. in the gas discharge is particularly suitable for plasma-induced NO production. In particular, limiting the temperature to less than 800° C. suppresses the damage to the electrode material (electrode erosion) caused by thermally formed oxygen radicals.

In accordance with a further mode of the invention, in order to effectively remove from the NO-enriched process gas nitrogen oxides in different oxidation states which are still produced in small amounts as a result of the gas discharge, they are catalytically reduced.

In accordance with an added mode of the invention, a gas temperature of up to 600° C. is advantageous during the reaction. Due to the reduction of the nitrogen oxides in different oxidation states, it is possible to limit the use of absorber materials, which need to be replaced frequently, to a minor extent.

In accordance with an additional mode of the invention, a high NO concentration in the process gas is advantageously produced through the use of the gas discharge and, if appropriate, the reduction carried out after it. The concentration is 1000 ppm, and thus exceeds the NO concentration of up to 200 ppm required for medical applications, by several times. The highly concentrated NO production is carried out with particularly high efficiency, and is thus energy-saving. In order to achieve an NO concentration in the process gas that is suitable for medical purposes, the process gas, which is highly enriched with NO, is diluted back by using untreated process gas, which thus has a low level of NO. The addition of the untreated process gas also leads to the highly enriched process gas being cooled. This further improves the cost-effectiveness of the method, not the least of which is in the way energy is saved for the cooling of the process gas, that is required in any case, before it is delivered to a patient.

In accordance with yet another mode of the invention, at least a portion of the excess heat in the process gas that has been enriched as a result of the gas discharge is recovered for preheating of the still untreated process gas. This reduces the operating costs for the cooling (which is required in any case) of the process gas flowing out of the discharge zone. The cooling that is achieved also largely suppresses undesirable secondary reactions in the process gas, such as the reformation of $NO_2$.

In accordance with yet a further mode of the invention, air is used as the process gas. This avoids complex handling of gas cylinders or similar storage measures. This is particularly advantageous when the method is used for mobile purposes. As an alternative to this, the use of so-called synthetic air is expedient, particularly when the method is carried out in a stationary environment, in the clinic area. This term means a mixture composed of nitrogen and oxygen, which are in each case present as pure gases. In this embodiment, the composition of the process gas can be varied, depending on the requirement. Since synthetic air is free of impurities and hazardous substances, there is no need to filter and clean the process gas before carrying out the method.

In accordance with yet an added mode of the invention, the NO production is controlled on basis of the volume flow of the process gas, the gas temperature and/or the discharge voltage as adjustment parameters. In this case the adjustment parameters may be used alternatively or simultaneously for controlling the NO production. The method can be advantageously optimized with regard to energy consumption and the production of undesirable byproducts, particularly when the NO production is controlled simultaneously through a plurality of adjustment parameters.

In accordance with yet an additional mode of the invention, the gas temperature, the gas pressure and at least the NO concentration are used as measurement variables for control purposes. The concentrations of $O_2$ and $NO_2$ are preferably also determined. The control process is carried out through the use of predetermined characteristics, which produce the relationship between the measurement variables and the adjustment variables. The measurement variables are advantageously determined in the diluted-back process gas, which is delivered as the end product to a patient. In this way, it is possible to use the measurement variables to particularly reliably monitor that the method is being carried out correctly. Any infringement of predetermined critical limits for the measurement variables, in particular the concentrations, is preferably indicated immediately, so that the further NO production can be stopped, if necessary.

With the objects of the invention in view there is also provided an apparatus for plasma-chemical production of nitrogen monoxide, comprising a plasma-chemical reactor for producing dielectric barrier discharges including an electrode; a dielectrically effective layer on the electrode; an opposing electrode opposite and at a distance from the electrode; mutually facing surfaces of the layer and the opposing electrode forming a discharge gap therebetween for conducting a flow of a process gas containing nitrogen and oxygen in a flow direction; and a number of constrictions forming discharge zones through which the process gas is passed in the flow direction and within which a dielectric barrier gas discharge is created, the gas discharge producing a non-thermal plasma having a gas temperature of at least 400° C. The surface of the electrode facing the discharge gap in this case is provided with a dielectric barrier, that is to say with a layer composed of a material with a dielectric effect.

The alternating constrictions subdivide the discharge gap along the flow direction into zones with a high electrical field for radical production, and into zones with a low electrical field for the radicals to react with the process gas, without any disturbance. Such structuring of the discharge gap results in a critical improvement in the efficiency of the reactor. At the same time, unlike corona electrodes in the form of wires or conventional cylindrical electrodes, it allows high electrical power levels to be injected without the discharge behaving in an uncontrolled manner and being drawn to a few points in the reactor, which are then extremely highly loaded. The gas discharge thus fulfills the purpose of raising the gas temperature in a controlled manner.

In accordance with another feature of the invention, in the discharge zones, the flashover distance, that is to say the width of the discharge gap in the region of each discharge zone, increases from discharge zone to discharge zone in the flow direction. This means that the same power level is always injected into the process gas, despite the successive heating of the gas along the reactor and the changes in the plasma conditions in each discharge zone resulting therefrom.

In accordance with a further feature of the invention, there is provided a catalytic converter downstream of the reactor, in the flow direction of the process gas, for reduction of nitrogen oxides in different oxidation states. If the converter is placed immediately adjacent the reactor in the flow direction, then this avoids the process gas cooling down between the reactor and the converter. The heat of the process gas, which has been heated as a result of the gas discharge, is thus used efficiently to accelerate the chemical reduction taking place in the converter.

In accordance with an added feature of the invention, further energy for heating, and subsequently cooling, the process gas, is saved by using a heat exchanger to preheat the process gas flowing to the reactor, with the heat being recovered from the process gas flowing out of the reactor.

In accordance with an additional feature of the invention, the converter is constructed integrally as a heat exchanger.

In accordance with yet another feature of the invention, there is provided a branch line which is connected in parallel with the reactor and the converter and also contributes to optimization of the energy consumption of the apparatus, with untreated process gas bypassing the reactor and the converter through this branch line. The reactor and the converter can thus be operated at particularly high efficiency, with the process gas flowing through the reactor and the converter being highly enriched with NO. This highly enriched process gas is diluted back to the desired NO concentration through the branch line, thus at the same time achieving energy-saving cooling of the highly enriched process gas.

In accordance with yet a further feature of the invention, there is provided a test probe disposed downstream of the converter in the flow direction of the process gas, the test probe having a temperature sensor, a pressure sensor and/or at least one sensor for determining a concentration in the process gas.

In accordance with yet an added feature of the invention, there is provided a control unit for adjusting a power coupled into the reactor, a volume flow of the process gas and/or a gas temperature.

In accordance with a concomitant feature of the invention, the apparatus produces nitrogen monoxide (NO) for medical purposes.

The advantages achieved by the invention are, in particular, that a plasma-chemical reactor for producing a dielectric barrier discharge can be used particularly effectively to produce nitrogen monoxide in a process gas containing nitrogen and oxygen. However, the reactor, which is known per se from International Publication No. WO97/03746, is not used in accordance with the purpose it is given therein to decompose NO and $NO_2$ but, instead, to produce pure nitrogen monoxide. The invention is thus advantageously suitable for medical purposes.

Other features which are considered as characteristic for the invention are set forth in the appended claims.

Although the invention is illustrated and described herein as embodied in an apparatus for plasma-chemical production of nitrogen monoxide, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
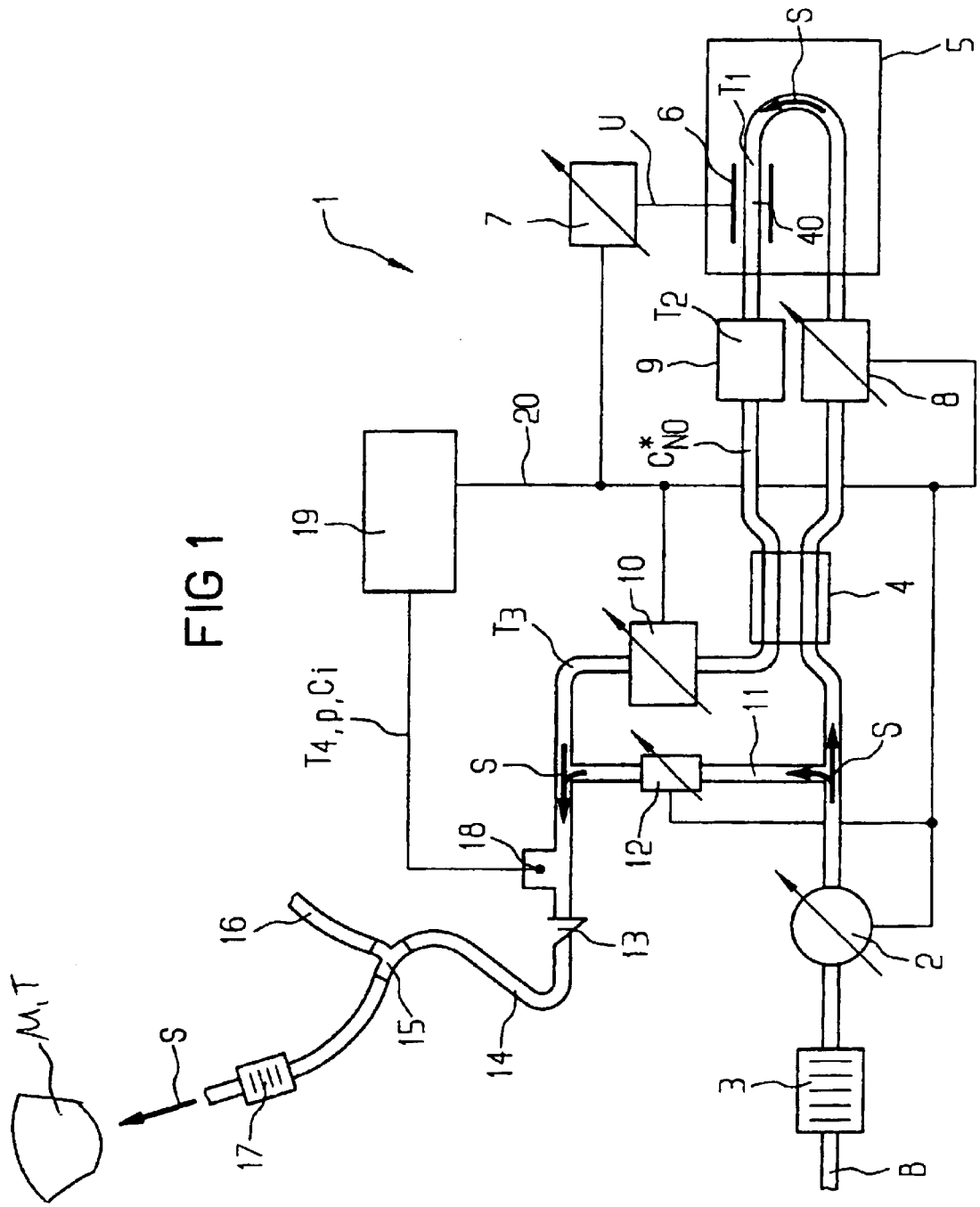
FIG. 1 is a schematic and diagrammatic view of an apparatus for producing nitrogen monoxide, in an embodiment intended for the use of air as a process gas.

Referring now to the figures of the drawings in detail and first, particularly, to FIG. 1 thereof, there is seen an apparatus 1 in which air is induced with a variable volume flow by a pump 2. The air is initially passed as a process gas B through an inlet filter 3 in which contaminating particles, such as soot or dust, are removed. Furthermore, the process gas B is preferably dried in the inlet filter 3.

The cleaned and dried process gas B is supplied, through the use of the pump 2, along a flow direction S and through a heat exchanger 4 to a plasma-chemical reactor 5.

The reactor 5 includes an electrode configuration 6 through which gas flows and which is supplied from a high-voltage power supply 7 with an adjustable discharge voltage U. A cyclic AC voltage at a frequency of between 1 kHz and 100 kHz and with a sinusoidal or pulsed waveform is used as the discharge voltage U. A mean discharge power is adjusted in this case through the amplitude and/or the frequency of the discharge voltage U. A non-thermal, spatially tightly confined, gas discharge is produced within the electrode configuration 6 as a result of the controlled supply of electrical power. The gas discharge predominantly produces nitrogen radicals in the process gas B, while at the same time heating the process gas B to a gas temperature $T_1$ of between 600° C. and 800° C. in the process. In addition, the process gas B can be heated further in a heating unit 8 connected upstream of the electrode configuration 6. This heating unit 8 is preferably constructed as a thermostatically controlled heating coil.

In the temperature interval, a nitrogen radical formed by the gas discharge reacts very efficiently with an oxygen molecule ($O_2$), forming NO. A decomposition reaction of the NO with an oxygen radical, forming $NO_2$, only takes place to a minor extent in this case, as a result of the comparatively high gas temperature $T_1$. The upper limit temperature for the gas discharge is selected on the basis of $T_1 \leq 800°$ C. in such a way that thermal NO production is avoided. Due to the involvement of oxygen radicals, such thermal NO production is associated with an extreme load on the reactor material.

A catalytic converter 9 is connected downstream of the reactor 5. The converter 9 is used to reduce nitrogen oxides in different oxidation states formed as a byproduct of the gas discharge, in particular $NO_2$ and $N_2O_5$ to NO. Japanese Patent Publication NO. 096-304377 discloses the use of $MO_2C$ with 1–2% Ni, for example, as a suitable catalyst material. This chemical reaction takes place particularly efficiently at a gas temperature $T_2$ of up to 600° C. The converter 9 is therefore disposed in the physical proximity of the reactor 5, in order to avoid the process gas B cooling down between the reactor 5 and the converter 9. The hot process gas B flowing out of the converter 9 is passed through the heat exchanger 4, in which a portion of its heat is recovered for preheating of the untreated process gas B flowing to the reactor 5. The process gas B flowing out of the reactor 5 is cooled down to an adjustable temperature $T_3$ (after it passes through the heat exchanger 4) in a cooler 10, which is preferably provided with a thermostat.

The reactor 5 and the converter 9 are used to enrich the process gas B to a high NO concentration $C_{NO}^*$, which exceeds values (<200 ppm) required for a medical application by several times. A branch line 11 is thus provided, which bridges the reactor 5 and the converter 9 and through which the highly enriched process gas B is diluted back, in terms of the NO content, by adding untreated process gas B. The addition of the untreated, and thus cold, process gas B at the same time further cools down the diluted-back process gas B in comparison with the highly enriched process gas B. The branch line 11 is provided with a mass-flow controller 12 in order to set a defined addition proportion. A valve which can be operated manually may also be provided, as a cost-effective alternative to this mass-flow controller 12.

The diluted-back process gas B flows through a nonreturn valve 13 (which opens in the flow direction S) into a preferably flexible line 14, that connects the apparatus 1 to an interface to a patient (for example a breathing mask M or an oxygen tent T). It is possible to further condition the diluted process gas B in a tee 15, which is disposed in the line 14, by adding air, oxygen, etc. through a supply line 16. An outlet filter 17 disposed downstream of the tee prevents $NO_2$ (which is formed in the meantime by a reaction of NO with $O_2$) from reaching the patient. This filter may contain known $NO_2$ absorbers such as NOXON, breathing lime, SODALIME, or SODASORB. The process gas B which is cleaned through the use of the outlet filter 17 is supplied to the patient as inhalation gas.

A test probe 18, around which the diluted process gas B flows, is disposed upstream of the nonreturn valve 13 and continuously monitors the process gas B. To this end, the test probe 18 is equipped with sensors for respectively measuring a temperature $T_4$, a pressure p and concentrations $C_i$ of NO, $O_2$ and $NO_2$ in the diluted process gas B. Preferably, electrochemical sensors are provided for concentration measurement, such as those normally used for flue-gas analysis. As an alternative to this, chemiluminescence sensors may also be used.

The temperature, pressure and concentration data $T_4$, p, $C_i$ determined by the test probe 18 are supplied as measurement variables to a central control unit 19. The control unit 19, which is preferably constructed as an electronic data processing system, is connected through a control line 20 to the pump 2, to the high-voltage power supply 7, to the heating unit 8, to the cooler 10 and to the mass-flow controller 12. The control unit 19 uses predetermined characteristics to control the devices 2, 7, 8, 10, 12 in such a manner that measured actual values of the measurement variables $T_4$, p, $C_i$ match externally predetermined nominal values. In the event of a critical error between the actual value and the nominal value of at least one measurement variable $T_4$, p, $C_i$, for example as a result of a defect in the apparatus 1, the control unit 19 emits an alarm signal and, if necessary, stops the NO production.

Figure 2:
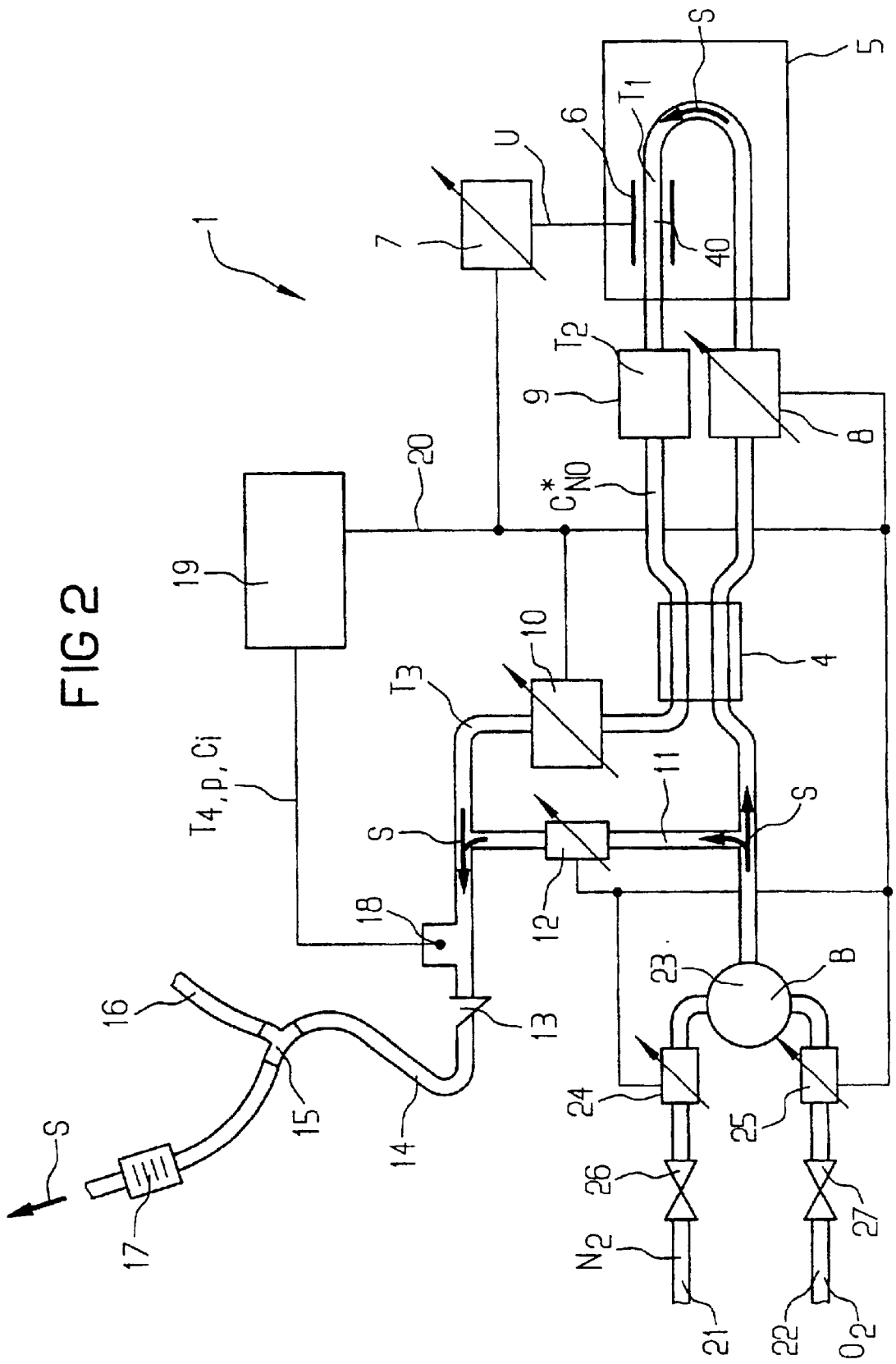
FIG. 2 is a schematic and diagrammatic view of an embodiment of the apparatus shown in FIG. 1, which is intended for the use of synthetic air as the process gas.

The embodiment of the apparatus 1 shown in FIG. 2 differs from the embodiment shown in FIG. 1 which is particularly suitable for mobile use, in that the embodiment of FIG. 2 is intended for the use of so-called synthetic air or of some other nitrogen/oxygen mixture as the process gas B. The term "synthetic air" in this context means a mixture of pure oxygen $O_2$ and pure nitrogen $N_2$ in a ratio of 2:8 (volume ratio). Since both gas components must be provided from gas cylinders, this embodiment of the apparatus 1 is primarily suitable for stationary use, for example in the clinic area.

When synthetic air is used, there is no need for the pump 2 or the inlet filter 3 shown in FIG. 1. Instead, the two gas components are combined through two separate supply lines 21 and 22 in a mixing chamber 23, and are thoroughly mixed, uniformly. The mixture ratio of the process gas B and its volume flow may be varied in this case through a respective mass-flow controller 24, 25 in each supply line 21, 22. The mass-flow controllers 24 and 25 in this case are likewise actuated from the central control unit 19, through the control line 20. In this case a respective control valve 26, 27 is connected upstream of each mass-flow controller 24, 25. Since the oxygen concentration is measured by the oxygen sensor in the test probe 18 and is reported to the control unit 19, any malfunction of the mass-flow controllers 24, 25 can be detected immediately.

The rest of the structure of the apparatus 1 corresponds to the exemplary embodiment shown in FIG. 1.

Figure 3:
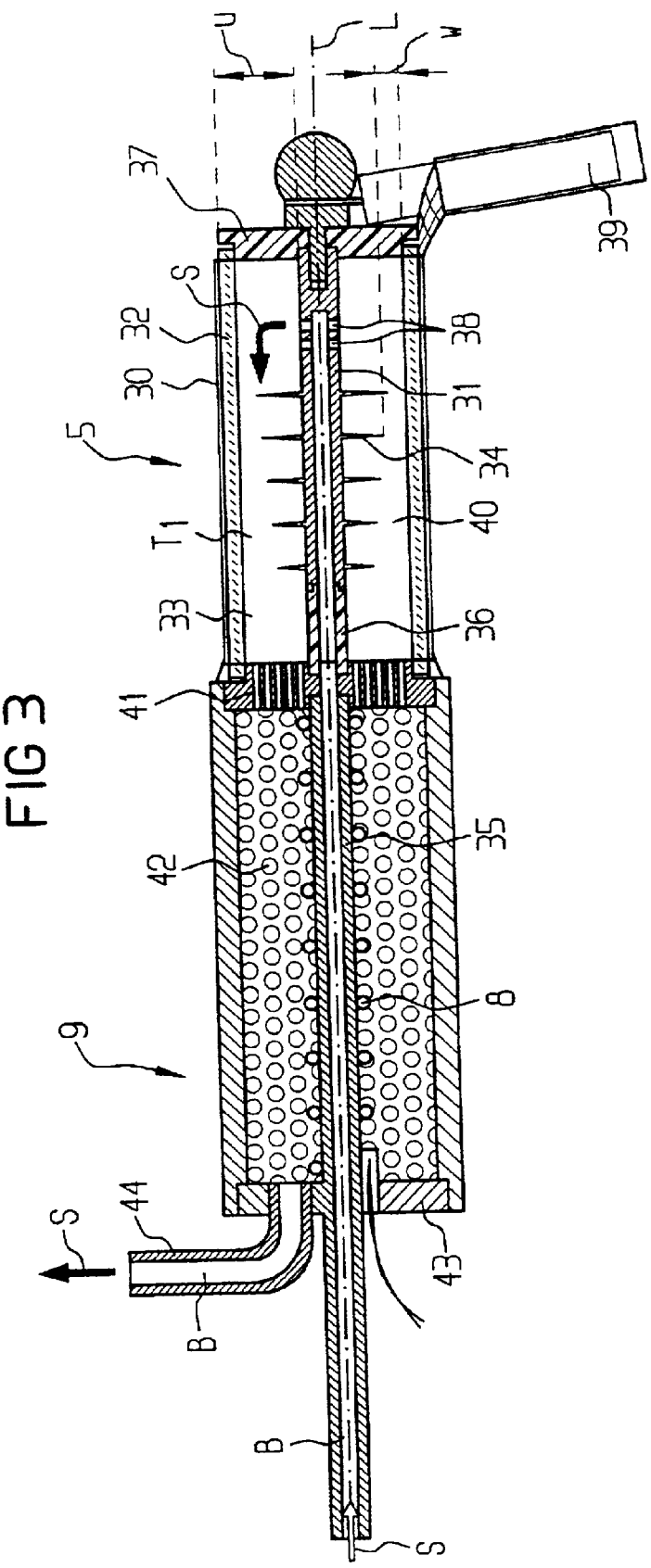
FIG. 3 is a longitudinal-sectional view of a plasma-chemical reactor having a catalytic converter fitted thereto.

FIG. 3 shows a preferred embodiment of the plasma-chemical reactor 5 and of the catalytic converter 9, according to which the converter 9 is fitted directly on the reactor 5. The reactor 5 and the converter 9 in this case have an essentially hollow-cylindrical shape, and are disposed coaxially with respect to a longitudinal axis L.

The electrode configuration 6 shown in FIGS. 1 and 2 is formed by an electrode 30 and an opposing electrode 31. The electrode 30, which is constructed as a hollow-cylindrical wall of the reactor 5, in this case is provided with a dielectric layer on the inside, as a barrier 32. Quartz glass or a densely sintered aluminum-oxide ceramic is preferably used in this case as the material for the barrier 32. The essentially hollow-cylindrical opposing electrode 31 in this case is held coaxially in the interior of the electrode 30. An annular space formed between the barrier 32 and the opposing electrode 31 is referred to as a discharge gap 33. The opposing electrode 31 has an outer surface which is fitted with a number of projections 34 in the form of annular disks, that project into the discharge gap 33 at right angles to the longitudinal axis L. The projections 34 thus constrict the discharge gap 33 alternately with respect to the longitudinal axis L.

The process gas B is supplied to the reactor 5 through the hollow opposing electrode 31. For this purpose, the opposing electrode 31 is connected to a pipeline 35, which is made of stainless steel, is aligned with the opposing electrode 31 and passes through the entire length of the converter 9. The pipeline 35 and the opposing electrode 31 in this case are electrically isolated from one another through the use of an adapter sleeve 36 made of insulating material. The process gas B supplied to the reactor 5 thus initially flows within the pipeline 35 through the converter 9 and, in the process, is preheated by the heating unit 8 that is disposed around the pipeline 35. The preheated process gas B is passed on within the opposing electrode 31 and emerges from this opposing electrode 31 through appropriate outlet openings 38, into the discharge gap 33. The process gas B emerges close to a free end of the reactor 5, which is closed by an end wall 37 made of insulating material. In the discharge gap 33, the process gas B flows back in the direction of the converter 9, passing constrictions which are formed by the projections 34.

As a result of the discharge voltage U, which is applied to the electrodes 30, 31 through a coaxial cable 39, a physically tightly confined discharge zone 40 is formed between an edge of each projection 34 which projects into the discharge gap 33 and a radially opposite region on the inner wall surface of the barrier 32. Molecules of the process gas B are ionized as they pass the discharge zone 40. A current flow is produced in the discharge zone 40 as a result of the ionization produced by the discharge voltage U.

Since the dielectric barrier 32 has poor electrical conductivity, the current flow results in a back emf building up locally between the inner wall surface of the barrier 32 and the electrode 30. In consequence, the voltage at this point falls below the voltage required to maintain the gas discharge after a short time, and suppresses further injection of energy.

Nitrogen radicals, in particular, are produced in the gas discharge, and react with oxygen to form NO. There is no discharge in the respective regions of the discharge gap 33 which are located between two discharge zones 40. The radical-induced production of the NO takes place in these discharge-free zones, without being disturbed by renewed ionization processes.

A flashover distance W is 2 to 4 mm. The flashover distance W in this case means the distance between each projection 34 and the barrier 32, or in other words the width of the discharge gap 33 in the region of each discharge zone 40. With a barrier thickness of about 5 mm, a discharge voltage U having a voltage amplitude which is about 3 kV is sufficient to ignite a gas discharge. The flashover distance W of the successive discharge zones 40 is increased successively in the flow direction S of the process gas B, as can be seen in FIG. 3. This takes into account the knowledge that the voltage to ignite a gas discharge falls as the gas temperature $T_1$ rises. In consequence, despite the successive gas heating of the process gas B flowing along the reactor 5, this results in roughly the same power being injected into the process gas B in each discharge zone 40.

After passing through the discharge zones 40, the process gas B passes through an end wall 41, which is permeable to the process gas B, into an adjacent internal space 42 of the converter 9. This internal space 42 is filled with a catalyst material, which catalytically assists the reduction of $NO_2$ or nitrogen oxides in higher oxidation states, to form NO. As a result of the coaxial configuration of the pipeline 35 and the heating unit 8 in the converter 9, the heating unit 8 also heats the catalyst material, thus accelerating the reduction. Conversely, the hot process gas B which flows through the internal space 42 heats the process gas B which is flowing in within the pipeline 35. In the version shown in FIG. 3, the converter 9 thus also carries out the function of the heat exchanger 4 shown in FIGS. 1 and 2, in an integral manner. The process gas B flowing out of the internal space 42 is passed to the cooler 10 (which is not shown in FIG. 3) through a gas outlet 44 which is disposed in an end wall 43 of the converter 9 that faces away from the reactor 5.

We claim:

1. An apparatus for plasma-chemical production of nitrogen monoxide for medical purposes, comprising:
    a plasma-chemical reactor for producing dielectric barrier discharges, said reactor including:
        an electrode, with a dielectrically effective layer;
        an opposing electrode;
        mutually facing surfaces of said layer and said opposing electrode forming a discharge gap therebetween for conducting a flow of a process gas containing nitrogen and oxygen in a flow direction;
        a number of constrictions forming discharge zones through which the process gas is passed in said flow direction and within which a dielectric barrier gas discharge is created, said reactor configured to produce said gas discharge having a non-thermal plasma with a gas temperature of at least 400° C.; and
        a reactor outlet; and
    an interface connected to said reactor outlet to facilitate inhalation of gas, produced from said reactor, by a person.

2. The apparatus according to claim 1, wherein said discharge gap has a width in each of said discharge tones increasing from discharge zone to discharge zone in said flow direction of the process gas.

3. The apparatus according to claim 1, including a converter disposed immediately downstream of said reactor in said flow direction of the process gas, said converter configured to catalytically reduce nitrogen oxides in different oxidation states produced as a result of the gas discharge, to nitrogen monoxide.

4. The apparatus according to claim 3, including a heat exchanger for preheating the process gas flowing to said reactor with the heat of the process gas flowing out of said reactor.

5. The apparatus according to claim 4, wherein said heat exchanger is integrated in said converter.

6. The apparatus according to claim 3, including a branch line connected in parallel with said reactor and said converter, for diluting back the highly nitrogen monoxide enriched process gas flowing out of said converter with untreated process gas.

7. The apparatus according to claim 3, including a test probe disposed downstream of said converter in said flow direction of the process gas, said test probe having at least one of a temperature sensor, a pressure sensor and at least one sensor for determining a concentration in the process gas.

8. The apparatus according to claim 1, including a control unit for adjusting at least one of a power coupled into said reactor, a volume flow of the process gas and a gas temperature.

9. The apparatus according to claim 1, wherein said interface is selected from the group consisting of a breathing mask and an oxygen tent.

10. The apparatus according to claim 1, wherein the gas to be inhaled by a person is nitrogen monoxide.

11. An apparatus for plasma-chemical production of nitrogen monoxide for medical purposes, comprising:
    a plasma-chemical reactor for producing dielectric barrier discharges, said reactor including:
        an electrode with a dielectrically effective layer;
        an opposing electrode;
        mutually facing surfaces of said layer and said opposing electrode forming a discharge gap therebetween for conducting a flow of a process gas containing nitrogen and oxygen in a flow direction;
        a number of constrictions forming discharge zones through which the process gas is passed in said flow direction and within which a dielectrically impeded gas discharge is created, said reactor configured to produce a gas discharge having a non-thermal plasma with a gas temperature of at least 400° C.; and
        a reactor outlet; and
    an interface connected to said reactor outlet to facilitate inhalation of gas, produced from said reactor by a person.

* * * * *